United States Patent

Bahr et al.

[11] Patent Number: 5,869,185
[45] Date of Patent: Feb. 9, 1999

[54] COATINGS USEFUL FOR ABSORBING ULTRAVIOLET LIGHT

[75] Inventors: Steven Roger Bahr, Niskayuna; James Edward Pickett, Schenectady; Karen Kueck Webb, Ballston Lake, all of N.Y.

[73] Assignee: General Electric Company, Schenectady, N.Y.

[21] Appl. No.: 669,899

[22] Filed: Jun. 21, 1996

Related U.S. Application Data

[63] Continuation of Ser. No. 355,001, Dec. 16, 1994, abandoned, which is a continuation-in-part of Ser. No. 205,478, Mar. 4, 1994, abandoned.

[51] Int. Cl.$^6$ .......................... B32B 27/08; B32B 27/18; B32B 27/30; B32B 27/36
[52] U.S. Cl. .......................... 428/412; 428/331; 428/447; 428/451; 428/522; 524/323; 524/330; 524/333; 524/335; 524/337; 524/343; 524/344; 524/345; 524/346; 524/348
[58] Field of Search .................................. 428/331, 412, 428/447, 451, 203; 524/335, 337, 344, 345, 346, 348, 323, 330, 333, 343

[56] References Cited

U.S. PATENT DOCUMENTS

| | | | |
|---|---|---|---|
| 2,852,488 | 9/1958 | Clark et al. | 260/45.9 |
| 2,861,976 | 11/1958 | Gordon | 260/45.95 |
| 2,900,361 | 8/1959 | Havens | 260/45.95 |
| 4,177,213 | 12/1979 | Schmidt | 260/590 R |
| 4,284,685 | 8/1981 | Olson et al. | 428/331 |
| 4,382,109 | 5/1983 | Olson et al. | 428/331 |
| 4,395,461 | 7/1983 | Ching | 428/412 |
| 4,486,565 | 12/1984 | Benjamin | 524/506 |
| 4,495,360 | 1/1985 | Anthony | 556/436 |
| 5,041,313 | 8/1991 | Patel | 427/379 |
| 5,391,795 | 2/1995 | Pickett | 556/436 |

FOREIGN PATENT DOCUMENTS

| | | |
|---|---|---|
| 567966 | 12/1958 | Canada . |
| 1251020 | 9/1967 | Germany . |
| 1518148 | 12/1969 | Germany . |
| 55-135159 | 10/1980 | Japan . |
| 2072942 | 3/1990 | Japan . |

*Primary Examiner*—Vivian Chen
*Attorney, Agent, or Firm*—Noreen C. Johnson; Douglas E. Stoner

[57] ABSTRACT

A polycarbonate substrate coated with an acrylic coating containing at least one polybenzoylresorcinol, and optionally a silicone hardcoat on the acrylic coating, wherein said at least one polybenzoylresorcinol has the formula

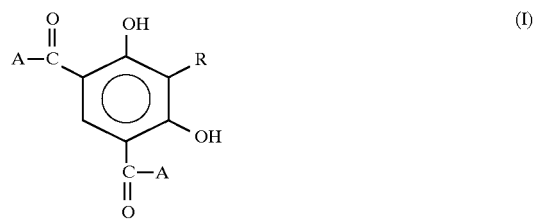

(I)

or

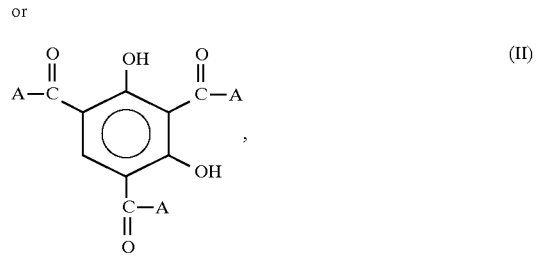

(II)

wherein each A is independently a substituted or unsubstituted monocyclic aromatic radical wherein any substituents are hydrogen, halogen, alkoxy, $C_{1-8}$ alkyl, or hydroxy, and R is hydrogen or a linear or branched aliphatic radical having less that about 10 carbon atoms.

20 Claims, No Drawings

COATINGS USEFUL FOR ABSORBING ULTRAVIOLET LIGHT

CROSS REFERENCE TO RELATED APPLICATIONS

This application is a continuation of application Ser. No. 08/355,001, filed Dec. 16, 1994, abandoned, which in turn is a continuation-in-part of application Ser. No. 08/205,478, filed Mar. 4, 1994, abandoned.

FIELD OF THE INVENTION

This invention relates to compounds capable of absorbing ultraviolet light. More particularly, the compounds are polybenzoylresorcinols which are photostable and compatible in coatings which may be employed as ultraviolet protective layers, as well as primers for silicone hardcoats and the like.

BACKGROUND OF THE INVENTION

Thermoplastic resins are generally characterized by their many advantageous properties which include optical clarity, high ductility, high heat deflection temperature as well as dimensional stability. As a result of such properties, they are often employed in many commercial applications.

While thermoplastic resins possess the above-described advantageous properties, they often display low abrasion and chemical solvent resistances, and like many other organic polymeric materials, they are susceptible to photodegradation by ultraviolet light. The photodegradation typically results in unfavorable characteristics including yellowing and erosion of the polymer surface.

It is of increasing interest to prepare thermoplastic resins, particularly polycarbonates, that are resistant to abrasion and photodegradation. Such preparation conventionally employs treating the polycarbonate surface with a coating material, whereby the coating material typically contains ultraviolet light absorbing agents such as cyanoacrylate, benzophenone and benzotriazole derivatives.

It is often discovered, however, that the ultraviolet light absorbing agents, themselves, decompose upon exposure to ultraviolet light. This invariably leads to a degradation of the favorable properties of the thermoplastic resin which the agents are originally employed to protect. Additionally, the ultraviolet absorbing agents often have poor compatibility in the coating material which limits the amount which may be employed in the coating.

Moreover, it is further discovered that a number of coating materials do not adhere to the thermoplastic resins with a great deal of ease. To compensate for this, primers are often employed to promote the adhesion of the coating materials to the thermoplastic resins. Thus, it is important for the primers to be clear and colorless and they must adhere to the thermoplastic resins and coating materials without diminishing any of their favorable properties.

The instant invention, therefore, is directed to novel coatings which may also be employed as ultraviolet protective layers as well as primers for silicone hardcoats and the like. The novel coatings comprise photostable polybenzoylresorcinols and they are capable of absorbing ultraviolet light.

DESCRIPTION OF THE PRIOR ART

Efforts have been disclosed for preparing primers and substituted resorcinols. In commonly assigned U.S. Pat. No. 4,410,594, acrylic polymer containing primer solutions which comprise hydroxy ethers, alkanols or mixtures thereof and water are disclosed.

Additionally, in U.S. Pat. No. 2,794,052, a process for preparing 4,6-dibenzoylresorcinol is disclosed, whereas in U.S. Pat. No. 2,861,976, dibenzoylresorcinols are disclosed as stabilizers for haloethylene polymers.

The instantly claimed invention is patentably distinguishable from the above-described since, among other reasons, it is directed to novel coatings which comprise photostable polybenzoylresorcinols capable of absorbing ultraviolet light. Further, said novel coatings may be employed as primers for promoting adhesion of silicone hardcoats and the like to thermoplastic resins.

The novel coatings of this invention unexpectedly display improved weatherabilities as depicted by their Yellowness Indices. Additionally, said novel coatings unexpectedly retain at least about 90% of the total polybenzoylresorcinols added subsequent to curing the coating at 100° C. for 1 hour. Thus, less than 10% of the total polybenzoylresorcinols added in the coating materials/primers volatilizes and/or migrates to the solid substrate after curing.

Still another unexpected superior result observed in the instant invention is the fact that no haze/crystallization is observed in the coating when up to about 50% by weight of polybenzoylresorcinol is employed based on total weight of the coating and said 50% by weight of polybenzoylresorcinol has both polybenzoylresorcinols as represented by formulae I and II below.

Moreover, as used throughout, photostable is defined as having a rate of photodegradation exhibiting a loss of less than about 0.75 and preferably less than 0.1 and most preferably less than about 0.05 absorbance units/1000 hr. xenon arc exposure as described in Pickett et al., *Polymer Degradation and Stability*, 42, pp. 231–244 (1993).

SUMMARY OF THE INVENTION

In a first aspect, the instant invention is directed to novel coating compositions that are photostable and capable of absorbing ultraviolet light.

The novel coating compositions comprise:

(a) at least one polybenzoylresorcinol having the formulae

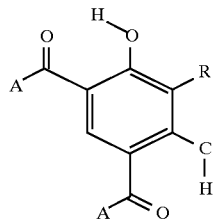

I or

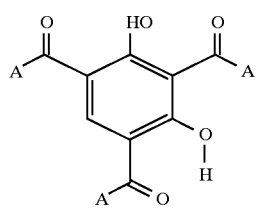

II wherein each A is independently a substituted or unsubstituted monocyclic or polycyclic aromatic radical, and said substituted monocyclic or polycyclic aromatic radical has substituents selected from the group consisting of hydrogen, halogens, alkoxy groups, $C_{1-8}$ alkyl groups and hydroxy groups and R is hydrogen or a linear or branched aliphatic chain having less than about 10 carbons; and (b) a transparent polymer matrix compatible with the polybenzoylresorcinols represented by formulae I and II.

Often, the preferred polybenzoylresorcinols are 4,6-dibenzoylresorcinol, 4,6-di-(4'-t-butylbenzoyl) resorcinol, 4,6-dibenzoyl-2-propylresorcinol and 2,4,6-tribenzoylresorcinol.

Moreover, in the instant invention it is often typical that the novel coatings comprise at least about 50% by weight of the polybenzoylresorcinol represented by formula I and preferably at least about 65% by weight of the polybenzoylresorcinol represented by formula I and most preferably at least about 75% by weight of the polybenzoylresorcinol represented by formula I based on total weight of polybenzoylresorcinol in the coating when both formulae I and II are employed.

Compatible, as used throughout, is defined as meaning a polymer matrix combined with the polybenzoylresorcinols of formula I and/or formula II, wherein phase separation of the polybenzoylresorcinols from the polymer matrix is not prominent.

In view of this, there are no limitations with respect to the transparent polymer matrices that may be employed in the instant invention other than that they are, again, compatible with the above-described polybenzoylresorcinols. Illustrative examples of the transparent polymer matrices that may be employed in the instant invention include polyurethanes, polycarbonates, polystyrenes, acrylic or methacrylic polymers or copolymers as well as mixtures thereof. As used throughout, acrylic polymers may be defined as acrylates, methacrylates as well as copolymers and mixtures thereof. Also included in the term polymer matrix are compositions that typically comprise acrylic polymers and organic solvents as well as emulsions of acrylic polymers and water and acrylic polymer compositions in water. When emulsions are employed, the polybenzoylresorcinols are dispersed therein. Stabilization of the resulting emulsions is achieved by, for instance, employing silylated polybenzoylresorcinols or by employing low melting point mixtures of polybenzoylresorcinols, such mixtures include mixtures of formula I, mixtures of formula II and mixtures of formula III. Low melting point as used herein is defined to mean a melting point low enough to prevent crystallization of the polybenzoylresorcinols in the emulsion and it is often a melting point of less than about ambient temperature. Said silylation can be achieved by subjecting an olefin-containing polybenzoylresorcinol to trialkoxysilanes and a hydrosilylation catalyst and said mixture of polybenzoylresorcinol is obtained by, for example, using a mixture of benzoyl chloride derivatives during a Friedel Crafts acylation. The often preferred transparent polymer matrix is poly(methyl methacrylate).

In a second aspect, the instant invention is directed to solid substrates comprising the above-described novel coatings as primers for silicone hardcoats and the like.

DETAILED DESCRIPTION OF THE PREFERRED EMBODIMENTS

Preparation of the polybenzoylresorcinols of the instant invention is achieved, for instance, by first reacting a benzoyl halide and an aluminum halide in an organic solvent with a dialkoxybenzene to produce the desired polybenzoylresorcinol. Said preparation is further illustrated by the following examples. Molecular structures of all products in the examples may be confirmed by proton and carbon-13 nuclear magnetic resonance spectroscopy.

EXAMPLE 1

A 500 mL 3-necked flask fitted with a gas scrubber, thermometer and magnetic stirrer was charged with 28.1 g (200 mmol) of benzoyl chloride and 100 mL of methylene chloride to produce a solution. The solution was cooled to 5° C. and 27.0 g (203 mmol) of anhydrous aluminum chloride were added in two portions keeping the temperature below 20° C. The resulting mixture was cooled to 5° C. 13.8 g (100 mmol) of 1,3-dimethoxybenzene were added dropwise over the course of about 30 minutes and the temperature was kept below 10° C. The mixture was stirred for about 1 hour at room temperature and subsequently heated to reflux. After heating overnight, the mixture was cooled and 20 mL of concentrated HCl were added dropwise. 100 mL of water and 50 mL of methylene chloride were then added and the resulting aqueous and organic phases were separated. The organic phase was evaporated to dryness and the resulting solid was recrystallized two times from a boiling ethanol/toluene mixture. 16.21 g (51%) of 4,6-dibenzoylresorcinol were recovered. Ultraviolet spectrum indicated ($CHCl_3$) :$\lambda_{max}$ 279 nm ($\epsilon$=29,100), 330 nm (shoulder, $\epsilon$=8,800).

EXAMPLE 2

Example 2 was prepared in a manner similar to Example 1 except that 39.3 g of p-tert-butylbenzoyl chloride was used in lieu of benzoyl chloride. 19.8 g (46%) of 4,6-di-(4'-t-butylbenzoyl)resorcinol was recovered.

EXAMPLE 3

A round bottomed flask equipped with a reflux condenser and magnetic stirrer was charged with 6.36 g (10 mmol) and 22 mL of 1.0N aqueous NaOH. 63 mg of tetrabutylammonium bromide and 10 mL of allyl chloride were added to produce a mixture. The mixture was stirred vigorously and heated at reflux for 5 hours. Excess allyl chloride was distilled and recovered, and 1 mL of 5% aqueous HCl was added to neutralize any base. The resulting solid was filtered and recrystallized from an ethanol/chloroform mixture to yield 4.8 g (67%) 4,6-dibenzoyl-2-allylresorcinol. The allyl compound was subjected to catalytic hydrogenation at atmospheric pressure using a 5% platinum on a carbon catalyst in an ethanol/toluene solvent mixture to produce 4.8 g of 4,6-dibenzoyl-2-propylresorcinol. Ultraviolet spectrum indicated ($CHCl_3$):$\lambda_{max}$288 nm ($\epsilon$=27,900), 330 nm (shoulder) ($\epsilon$=7000).

EXAMPLE 4

A 500 mL three-necked flask equipped with a magnetic stirbar, 50 mL addition funnel, thermometer and condenser attached to an oil bubbler and gas scrubber was charged with 52.7 g (375 mmol) of benzoyl chloride and 75 mL of methylene chloride to produce a mixture. The mixture was cooled to less than about 5° C. with an ice bath and 42 g (315 mmol) of aluminum chloride were subsequently added in three portions producing a reaction mixture of a temperature below 15° C. The reaction mixture was stirred for 30 minutes at a temperature of 5° C. and 13.8 g (100 mmol) of 1,3-dimethoxybenzene were added dropwise from the addition funnel over a 30 minute period keeping the reaction temperature less than about 10° C. The reaction mixture was subsequently warmed to 30° C. over 2 hours by means of a water bath during which significant amounts of gaseous products were liberated for several hours at this temperature. Subsequent to stirring the reaction mixture for 4 days, an additional 100 mL of methylene chloride was added and the reaction mixture was slowly poured into an ice cooled mixture of 50 mL concentrated HCl and 200 mL water producing a two phase reaction mixture. Methylene chloride was added to the two phase reaction mixture until the entire mixture was in solution. Subsequently the phases were separated into an aqueous phase and organic phase. The aqueous portion was extracted with another 50 mL of methylene chloride and all organic portions were combined and evaporated to dryness. A yellow product was obtained which was recrystallized twice by dissolving in methylene chloride and precipitating by addition of absolute ethanol. 24.7 g (58% yield) of light yellow 2,4,6-tribenzoylresorcinol were recovered. Ultraviolet light spectrum indicated (CHCl$_3$: $\lambda_{max}$ 278 nm ($\epsilon$=35,500), 330 nm ($\epsilon$=9280).

While the often preferred polymer matrix employed in the instant invention is poly(methyl methacrylate), additional transparent polymer matrices that may be employed in this invention include acrylic polymers/copolymers having reactive functional groups which are capable of reacting between themselves to effect a cross-linkage thereof, acrylic polymers/copolymers having reactive functional groups to which is added an appropriate cross-linking agent which will react with the functional groups to effect cross-linking and a mixture of two polymers having crosslinkable functional reactive groups.

The reactions involved in cross-linking the acrylic polymers are reactions between, for example, epoxide functional groups and amine functional groups; epoxide functional groups and acid anhydride functional groups; epoxide functional groups and carboxyl functional groups, including phenolic hydroxyl groups; epoxide functional groups and N-methylol or N-methylol-ether groups; carboxyl functional groups and N-methylol or N-methylol-ether functional groups; interreaction between carboxyl and isocyanate groups; reactions between hydroxyl, for example polyols, and isocyanate groups; and reactions between amine groups and N-methylol or N-methylol-ether groups. In the case of resin mixtures, the acrylic will be present in a major proportion, i.e., greater than 50 weight percent and, more typically, will be present in an amount in excess of about 70 percent. The needed functional groups in the acrylic copolymer, which is the foundation of the acrylic polymer, are provided by employing in the copolymerization a monomer which supplies the needed reactive functional group into the polymer chain. Usually, this copolymerizable functional group-supplying monomer will be present in small amounts, that is, on the order of 25 weight percent or less, and typically, between about 1 and 20 weight percent of the monomer mass which is polymerized. Some non-limiting examples of these functional group supplying monomers include glycidyl acrylate, glycidyl methacrylate, allyl glycidyl ether, dimethylaminoethyl methacrylate, vinyl pyridine, tert-butylaminoethyl-methacrylate, maleic anhydride, itaconic anhydride, allyl alcohol, monoallyl ethers of polyols, hydroxyethyl methacrylate, hydroxypropyl methacrylate, hydroxypropyl acrylate, acrylamide, methacrylamide, maleamide, N-methylolmethacrylamide, vinyl isocyanate, allyl isocyanate. The additional monomer polymerized along with the monomer supplying the functional group is typically a lower (C$_{1-3}$) alkyl acrylic ester or mixtures thereof, e.g., methyl acrylate, ethyl acrylate, methyl methacrylate, ethyl methacrylate, styrene, or mixtures thereof, in an amount ranging from about 50 parts by weight to about 99 parts by weight and, more typically, from about 80 parts by weight to about 95 parts by weight based on total weight of the polymer.

The transparent polymer matrix compositions described above may be of several general types. For instance, one type contains acrylic polymer and a solvent. The solvent used for these compositions is an organic solvent which dissolves the acrylic polymer, is inert towards the solid substrate, and is readily volatilized. Some nonlimiting examples of such solvents include hydroxyethers, alcohols, keto alcohols, liquid aliphatic hydrocarbons, liquid cycloaliphatic hydrocarbons and mixtures thereof.

A second type of transparent polymer matrix composition that may be employed in the instant invention is one generally comprised of an emulsion of an acrylic polymer and water. These emulsions are commercially available and sold, for example, by the Rohm & Haas Company of Philadelphia, Pa., under the tradename Rhoplex® and B. F. Goodrich Company under the tradename Hycar®. Generally, these emulsions are in the form of emulsion concentrates which contain from about 40 to about 55% by weight solids. However, in formulating the emulsion compositions it is desirable that the emulsion composition contain from about 1 to about 10 weight percent solids. Thus, it is generally necessary to dilute these commercially available emulsion concentrates by the addition of additional water thereto. Such emulsion compositions may additionally contain a curing catalyst for the acrylic polymer. If such a catalyst is present it may be present in from about 0.05 to about 2 weight percent based on the weight of the acrylic polymer solids present. Examples of such catalysts include toluene sulfonic acid, citric acid, phosphoric acid, and the like.

Another type of transparent polymer matrix composition employed in the invention includes emulsions comprised of (i) from about 1 to about 10 weight percent of acrylic polymer solids; (ii) from about 20 to about 45 weight percent of a hydroxy ether, an alkanol, or a mixture of a hydroxy ether and an alkanol; and (iii) from about 45 to about 80 weight percent of water.

In this type of composition the acrylic polymer, as is the case with the commercially available emulsions described above, is generally in the form of discrete spherical particles (approximately 0.1 micron in diameter) dispersed in water. Since the polymer particles are separate from the continuous aqueous phase, the viscosity of the dispersion or emulsion is relatively independent of the polymer's molecular weight. Consequently the emulsion can contain polymers of high molecular weight and yet have a relatively low viscosity. The concentration of the acrylic polymer solids in this emulsion composition is generally important. This is true because some hardcoats when applied to acrylic primer layers derived from emulsion compositions containing less than about 1 or more than about 10 weight percent of an acrylic polymer generally tend to exhibit a marked decrease in durability of adhesion. This is especially true after exposure to weathering, and abrasion resistance relative to hardcoats applied to acrylic layers derived from emulsion compositions containing from about 1 to about 10 weight percent of a thermosettable acrylic polymer. Emulsion compositions containing from about 2 to about 6 weight percent of an acrylic polymer are often preferred.

The hydroxy ethers which are present in these emulsion compositions are compounds represented by the general formula $$R^3\text{—}O\text{—}R^4\text{—}OH \qquad \text{III}$$

wherein R$^4$ is a saturated divalent aliphatic radical, preferably one containing from 1 to about 6 carbon atoms, and R$^3$ is an alkyl radical or an alkoxy alkyl radical containing from 1 to about 6 carbon atoms.

The alkanols that may be present in the emulsion composition are those containing usually from 1 to about 4 carbon atoms.

The presence of such hydroxy ethers, alkanols, or hydroxy ether-alkanol mixtures in amounts of from about °to about 45 weight percent of the emulsion composition is typical for the satisfactory performance of the emulsion composition in forming an effective layer. If no hydroxy ether or alkanol is present, or if an amount of hydroxy ether or alkanol less than about 20 weight percent is present, the emulsion composition does not generally flow evenly over the solid substrate, i.e., there is uneven distribution of the emulsion composition over the substrate with excessive concentrations of the composition in certain areas and a dearth of the composition in other areas. This results in an unevenly distributed and non-uniform layer being formed which in turn results in inferior adhesion of the hardcoat as well as a streaked appearance of the final coated product. If excessive amounts of hydroxy ether or alkanol are present, i.e., amounts greater than about 45 weight percent, coagulation and precipitation of the acrylic polymer solids generally occurs.

Additionally, the transparent polymer matrices utilized in this invention may include thermoplastic acrylic polymers and thermosetting acrylic polymers such as those described in commonly assigned U.S. Pat. Nos. 4,382,109 and 5,041,313 the disclosures of which are incorporated herein by reference.

The following examples illustrate and facilitate the production of the coating material/primer of the instant invention.

EXAMPLE 5

A glass vial was charged with 1.0 g of poly(methyl methacrylate), 0.02 g of 4,6-dibenzoylresorcinol as prepared in Example 1 and 9.0 mL of chloroform to produce a mixture. The mixture was stirred resulting in a coating solution. The solution was spread on a glass plate with a 10 mil doctor blade producing a coated plate. The coated plate was air dried until solvent was evaporated and a 25 micron thick coating formed. The coating on the glass plate was subjected to a xenon arc weatherometer to determine a photodegradation rate of 0.03 absorbance units/1000 hr xenon arc exposure.

EXAMPLE 6

A reaction vessel was charged with 6 g of poly(methyl methacrylate), 0.6 g of 4,6-di-(4'-t-butylbenzoyl)resorcinol, 79.4 g of propylene glycol monomethyl ether and 14 g of diacetone alcohol to produce a mixture. The mixture was stirred to produce a coating solution.

EXAMPLE 7

5.0 g of the allyl compound prepared in Example 3 were dissolved in 20 ml of warm toluene. One drop of Karstedt's catalyst (complex of 1,3-divinyl-tetramethyldisiloxane with platinum) was added to produce a mixture. The mixture was heated to 80° C. and 5 ml of triethoxysilane were added. Heating continued for about 1 hour and the mixture was cooled to room temperature. A precipitate formed and was removed via filtration. The filtrate was filtered through silica gel which was washed with chloroform and evaporated under reduced pressure. 7.04 g (96%) of 4,6-dibenzoyl-2-(3-triethoxysilylpropyl)resorcinol were recovered of which 1 gram was dissolved in 18.4 g of 2-butoxyethanol with gentle warming. One drop of 1% aqueous HCl and 30 g of $H_2O$ were added to produce a mixture. The mixture was stirred and heated to approximately 40° C. to produce a solution. The solution was cooled to room temperature and 2.0 g of Hycar® 26237 and 2.0 g of Hycar® 26256 (trademarks of B. F. Goodrich) thermosettable acrylic emulsions were added to produce a mixture. The mixture was stirred for 30 minutes at room temperature to produce a coating solution comprising 33% of the resorcinol based on total solids.

EXAMPLE 8

Example 8 was prepared in a manner similar to the one described in Example 6 except that 0.6 g of tribenzoylresorcinol (as prepared in Example 4) were added in lieu of 4,6-di-(4'-t-butylbenzoyl)resorcinol.

EXAMPLE 9

Example 9 was prepared in a manner similar to the one described in Example 8 except that 1.19 g of 2,4,6-tribenzoylresorcinol were employed along with 3.07 g of 4,6-dibenzoylresorcinol.

In the instant invention, there are no limitations with respect to the solid substrates employed. Said solid substrates often include polymer substrates such as acrylic polymers including poly(methyl methacrylate), polyesters such as poly(ethylene terephthalate) and poly(butylene terephthalate), polyamides, polyimides, acrylonitrile-styrene copolymers, styrene-acrylonitrile-butadiene copolymers, polyvinyl chloride, polystyrene, blends of polystyrene and polyphenylene ethers, butyrates, polyethylene and the like. Moreover, said solid substrates may also include metal substrates, painted surfaces, glass, ceramics and textiles.

The preferred solid substrates employed in the instant invention are polycarbonates.

Said polycarbonates employed in the instant invention may comprise structural units of the formulae $$-O-A^1-O-\overset{O}{\underset{\|}{C}}- \quad \text{IV}$$

and $$-O-A^2-Y-A^3-O-\overset{O}{\underset{\|}{C}}-, \quad \text{V}$$

wherein V is a preferred subgenus of IV and $A^1$ is a divalent substituted or unsubstituted aliphatic, alicyclic or aromatic radical, preferably $-A^2-Y-A^3-$ wherein $A^2$ and $A^3$ are each independently a monocyclic divalent aromatic radical. Y is a bridging radical in which 1 to 4 atoms separate $A^2$ from $A^3$ and IV is a preferred subgenus of IV.

The $A^2$ and $A^3$ values may be unsubstituted phenylene or substituted derivatives thereof, illustrative substituents (one or more) being alkyl, alkenyl, alkoxy and the like. Unsubstituted phenylene radicals are preferred. Both $A^2$ and $A^3$ are preferably p-phenylene, although both may be o- or m-phenylene or one o- or m-phenylene and the other p-phenylene.

The bridging radical, Y, is one in which one or two atoms, preferably one, separate $A^2$ from $A^3$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred units of formula V are 2,2-bis(4-phenylene)propane carbonate units, which are derived from bisphenol A and in which Y is isopropylidene and $A^2$ and $A^3$ are each p-phenylene.

The material represented by formula VI $$HO—A^1—OH \qquad\qquad VI$$

is the source of structural units of formula IV above; $A^1$ is as previously defined.

Illustrative non-limiting examples of VI include:
2,2-bis(4-hydroxyphenyl)-propane (bisphenol A);
2,2-bis(3,5-dibromo-4-hydroxyphenyl)propane;
2,2-bis(3,5-dimethyl-4-hydroxyphenyl)propane;
1,1-bis(4-hydroxyphenyl)cyclohexane;
1,1-bis(3,5-dimethyl-4-hydroxyphenyl)cyclohexane;
1,1-bis(4-hydroxyphenyl)decane;
1,4-bis(4-hydroxyphenyl)propane;
1,1-bis(4-hydroxyphenyl)cyclododecane;
1,1-bis(3,5-dimethyl-4-hydroxyphenyl)cyclododecane;
4,4-dihydroxydiphenyl ether;
4,4-thiodiphenol;
4,4-dihydroxy-3,3-dichlorodiphenyl ether;
4,4-dihydroxy-3,3-dihydroxydiphenyl ether;
1,3benzenediol; and
1,4-benzenediol.

Other useful dihydroxyaromatic compounds which are also suitable for use in the preparation of the above copolycarbonates are disclosed in U.S. Pat. Nos. 2,999,835; 3,028,365; 3,334,154 and 4,131,575, all of which are incorporated herein by reference. The preferred bisphenol is 2,2-bis(4-hydroxyphenyl)propane (bisphenol A).

The polycarbonates (homopolycarbonates or copolycarbonates) employed in the instant invention may be prepared by reacting bisphenols with a carbonate source such as phosgene or dimethyl carbonate using conventional techniques. These include melt polymerization, interfacial polymerization and interfacial conversion with bischloroformate followed by polymerization. Chain termination agents such as phenol may also be employed.

The above-described novel coatings (irrespective of their preparation) are generally applied onto the surface of the solid substrate in substantially the same way, and after application are subjected to generally the same procedure to produce the solid polymer and polybenzoylresorcinol containing layer. A thin layer of the coating is applied onto the surface of the solid substrate by any of the well known methods such as spraying, dipping, flow-coating, roll-coating and the like. Generally the coating is applied in an amount sufficient to provide a cured layer of from about 0.01 to about 50 μm thick, and preferably from about 0.1 to about 10 μm thick. After the coating has been applied onto the solid substrate, substantially all of the volatile liquids present in the coating, e.g., organic solvents, water and hydroxy ether or alkanol are evaporated. This evaporation is accomplished by air drying or heating. The evaporation of substantially all of the liquid component of the coatings leaves deposited on the substrate surface an even and generally solid layer comprised of a polymer and a polybenzoylresorcinol. Residual solvent may be removed by heating although this is not always necessary for thermoplastic since air drying is often sufficient to remove the solvent. When heating is desired, the temperature range is often from about 90° C. to about 130° C. Coatings prepared using thermosettable polymers or emulsions generally are baked at about 90° C. to about 130° C. for about 15 to about 90 minutes to effect cure. The end result of this procedure is a solid coating or primer layer comprised of a polybenzoylresorcinol and polymer durably and tenaciously adhered to the surface of a solid substrate.

The following examples describe the coating of polycarbonate, the preferred solid substrate.

EXAMPLE 10

The coating solution as prepared in Example 6 was applied to a 4"×8"×⅛" polycarbonate (BPA) panel via flow coating. Subsequent to air drying for 30 minutes, the coated panel was baked at 100° C. for 1 hour. The panel was subjected to accelerated weathering in a Q-Panel QUV apparatus equipped with FS-40 lamps to determine the change in Yellowness Index (YI) as defined by ASTM D-1925. Results revealed a (YI) of 1.2 after 2205 hours of exposure, an unexpected superior result.

EXAMPLES 11 and 12

The coating solutions as prepared in Examples 8 and 9 were each applied to a 4"×8"×⅛" polycarbonate (BPA) panel via flow coating. Subsequent to air drying for 1 hour at 100° C., the optically defect free coated panels were weathered in a QUV apparatus analyzed for 1000 hours and no increases in yellowness indices were observed.

EXAMPLE 13

Example 13 was performed in a manner similar to the one described in Example 12 except that no 2,4,6-tribenzoylresorcinol was employed. A hazy coating was observed after drying for 1 hour at 100° C.

There is no limitation with respect to the type of silicone hardcoats employed in this invention other than that they adhere to the novel coating/primer. Therefore, coatings prepared from basic, neutral or acidic colloidal silica may be used. Examples of the silicone hardcoats that may be employed when the novel coatings of the instant invention are employed as primers include those prepared by hydrolyzing an aqueous dispersion of colloidal silica and a trialkoxysilane or mixtures of trialkoxysilanes having the formula $$RSi(OR)_3, \qquad\qquad VI$$

wherein each R is independently an alkyl group having 1 to 3 carbon atoms or a substituted or unsubstituted aromatic radical; preferably, a methyl group.

It is also within the scope of the instant invention to include conventional additives such as compatible ultraviolet light absorbing agents, and polysiloxane polyether copolymers and the like in the silicone hardcoat resin since such additives have been found to reduce the incidence of stress cracking in the hardcoat. Other additives including thickening agents, pigments, dyes and the like may also be included for their conventionally employed purposes.

A detailed description for the preparation of silicone hardcoats suitable for this invention may be found in commonly assigned U.S. Pat. No. 4,373,061, the disclosure of which is incorporated herein by reference.

Examples 14 and 15 have been prepared to demonstrate that the novel coating compositions of the instant invention may be employed as primers for silicone hardcoats and the like.

EXAMPLE 14

A coated polycarbonate panel as prepared in Example 10 was flow coated with a silica resin (condensed methyl trimethoxy silane/aqueous colloidal silica resin at approximately 20% solids in an alcohol solvent) to produce a panel with a hardcoat. The panel was air dried for 15 minutes and subsequently cured at 100° C. for 90 minutes. The panel was subjected to accelerated weathering in a Q-Panel QUV apparatus using FS-40 lamps. Results revealed a change in Yellowness Index (YI) of 0.8 after 2205 hours of exposure, an unexpected superior result.

EXAMPLE 15

A coated polycarbonate panel was prepared in a manner similar to the one described in Example 10 except that the coating employed was an emulsion composition as prepared in Example 7. The coated polycarbonate panel was flow coated with a silica resin as described by Example 8 to produce a well adhered transparent abrasion resistant hardcoat.

Example 16 has been prepared to demonstrate an emulsion prepared with a low melting point mixture of polybenzoylresorcinols.

EXAMPLE 16

A complex mixture of resorcinols was prepared in a manner similar to the one described in Example 1 except that 3.15 g (25 mmol) of benzoyl chloride and 3.83 g (25 mmol) of 3-methylbenzoyl chloride were employed in lieu of only benzoyl chloride. 6.65 g (50 mmol) of anhydrous aluminum chloride, 3.45 g (25 mmol) of 1,3-dimethoxybenzene and 25 mL of methylene chloride were also employed in the same manner as Example 1. 8 g of a non-crystalline product were obtained. NMR spectroscopy revealed a complex mixture of dibenzoylresorcinols, tribenzoylresorcinol and monobenzoylresorcinol in the mixture product.

0.5 g of the above mixture was dissolved in 9.2 g of 2-butoxyethanol by warming. 15.0 g of water was added and the mixture was stirred until it reached room temperature at which time it was homogeneous. A mixture of 1.0 g of Hycar® 26256 and Hycar® 26237 acrylic emulsions was added with vigorous stirring. The resulting stable emulsion was flow coated onto a polycarbonate panel, air dried for 1 hour and baked at 105° C. for 30 minutes to produce a coating. This panel was then flow coated with a silicone hardcoat solution, air dried for 30 minutes and baked at 105° C. for 1 hour to produce a well-adhered and substantially optically defect-free coating.

The data in the following tables has been compiled to demonstrate the new and unexpected superior properties of the coating materials/primers described in the instant invention when compared with coatings prepared using UV absorbers commonly employed in the art. Entries 1 and 3 are dibenzoylresorcinols as described by formula I, Entry 2 is a tribenzoylresorcinol as described by formula II and Entries 4–8 are art recognized UV absorbing agents.

The following structures correspond to the entries in the tables hereinbelow.

| Entry | |
|---|---|
| 1 | 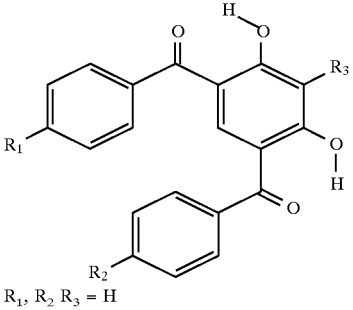 $R_1, R_2, R_3 = H$ |
| 2 | 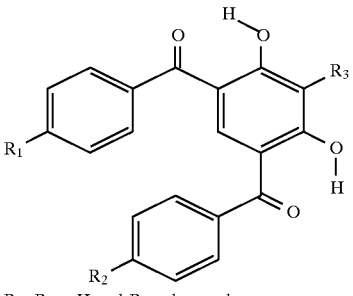 $R_1, R_2 = H$ and $R_3 =$ benzoyl |
| 3 | 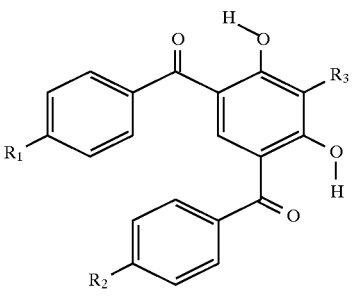 $R_1, R_2 = $ t-butyl, $R_3 = H$ |
| 4 (Comparative) | 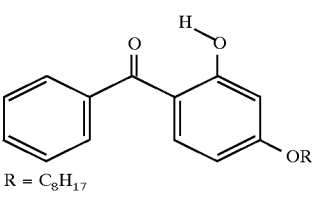 $R = C_8H_{17}$ |
| 5 (Comparative) | 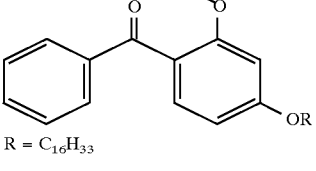 $R = C_{16}H_{33}$ |
| 6 (Comparative) | 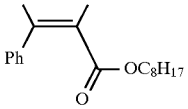 |

-continued

| Entry | |
|---|---|
| 7 (Comparative) | 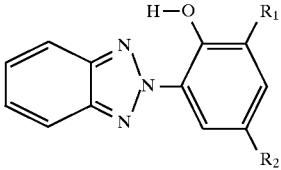<br>$R_1 = H, R_2 = C_8H_{17}$ |
| 8 (Comparative) | 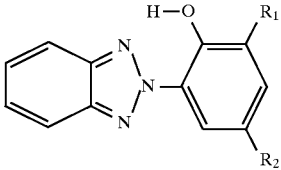<br>$R_1, R_2 = C(CH_3)_2Ph$ |

What is claimed is:

1. An article comprising a polycarbonate substrate coated with a coating composition comprising:

(a) at least one polybenzoylresorcinol having the formula

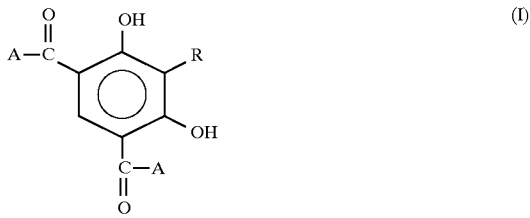

or

TABLE 1

| | 100° C. Cure | | | 130° C. Cure | | |
|---|---|---|---|---|---|---|
| Entry | % lost to volatility | % Remaining in transparent polymer matrix | % Migration to solid substrate | % lost to volatility | % Remaining in transparent polymer matrix | % Migration to solid substrate |
| 1 | 0 | 92 | 8 | 12 | 56 | 32 |
| 2 | 2 | 93 | 5 | 2 | 86 | 12 |
| 3 | 1 | 98 | 1 | 4 | 83 | 13 |
| 4 (Comparative) | 6 | 75 | 19 | 26 | 24 | 50 |
| 5 (Comparative) | 2 | 78 | 20 | 9 | 43 | 49 |
| 6 (Comparative) | 2 | 74 | 24 | 22 | 51 | 26 |
| 7 (Comparative) | 2 | 87 | 11 | 17 | 54 | 29 |
| 8 (Comparative) | 2 | 96 | 3 | 3 | 82 | 15 |

TABLE II

| | Yellowing Index 100° C. cure | | Yellowing Index 130° C. cure | | Rate of Photodegradation |
|---|---|---|---|---|---|
| Entry | No hardcoat | Silicone hardcoat | No hardcoat | Silicone hardcoat | Absorbance/1000 hr xenon arc exposure |
| 1 | 0.9 | 0.7 | 1.1 | 0.8 | 0.03 |
| 2 | — | — | — | — | 0.04 |
| 3 | 1.2 | 0.8 | 1.0 | 0.6 | 0.04 |
| 4 (Comparative) | 11.3 | 5.1 | >27.9[B] | 9.5 | 0.45 |
| 5 (Comparative) | 12.3 | 15.5 | >8.2[B] | 11.2 | — |
| 6 (Comparative) | 14.2 | 13.3 | 14.4 | 15.6 | 0.34 |
| 7 (Comparative) | 2.3 | 2.3 | 3.3 | 3.4 | 0.31 |
| 8 (Comparative) | 4.4 | 5.2 | 4.6 | 5.0 | — |
| 9[A] (Control) | >14.2 | >14.4 | >14.1 | >14.3 | — |

[A]Coatings failed by delamination at 884 hours.
[B]Coatings failed by delamination at 1537 hours.

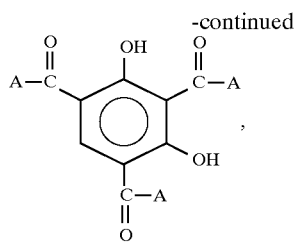

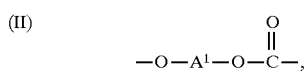

wherein each A is independently a substituted or unsubstituted monocyclic aromatic radical wherein any substituents are hydrogen, halogen, alkoxy, $C_{1-8}$ alkyl or hydroxy, and R is hydrogen or a linear or branched aliphatic radical having less than about 10 carbon atoms; and (b) a transparent polymer matrix compatible with said polybenzoyl resorcinols, said polymer matrix being selected from the group consisting of acrylic and methacrylic polymers and copolymers.

2. An article according to claim 1, wherein said polybenzoylresorcinols are 4,6-dibenzoylresorcinol, 4,6-di-(4'-t-butylbenzoyl)resorcinol, 4,6-dibenzoyl-2-propylresorcinol or 2,4,6-tribenzoylresorcinol.

3. An article according to claim 1 wherein said transparent polymer matrix is poly(methyl methacrylate).

4. An article according to claim 1 wherein said coating composition comprises acrylic polymers and organic solvents.

5. An article according to claim 1 wherein said transparent polymer matrix is an emulsion comprising acrylic polymers and water and said polybenzoylresorcinols are silylated; or are mixtures of formula I and formula II; or are both silylated and are mixtures of formula I and formula II.

6. An article according to claim 1 wherein said polycarbonate is a homopolycarbonate.

7. An article according to claim 1 wherein said polycarbonate is a copolycarbonate.

8. An article according to claim 1 wherein said polycarbonate comprises structural units of the formula wherein $A^1$ is a divalent substituted or unsubstituted aliphatic, alicyclic or aromatic radical.

9. An article according to claim 8 wherein $A^1$ has the formula $-A^2-Y-A^3-$, wherein each of $A^2$ and $A^3$ is a divalent aromatic radical and Y is a bridging radical.

10. An article according to claim 9 wherein said polycarbonate is a bisphenol A polycarbonate.

11. An article according to claim 1 wherein said coating is a primer having a silicone hardcoat applied thereon.

12. An article according to claim 11 wherein said silicone hardcoat comprises colloidal silica and a trialkoxysilane having the formula $R-Si(OR)_3$, wherein each R is independently a $C_{1-3}$ alkyl radical or an aromatic radical.

13. An article according to claim 12 wherein R is methyl.

14. An article according to claim 13 wherein said silicone hardcoat contains an ultraviolet light absorbing agent.

15. An article according to claim 1 wherein the polybenzoylresorcinol has formula I.

16. An article according to claim 1 wherein the polybenzoylresorcinol has formula II.

17. An article according to claim 1 wherein the polybenzoylresorcinols are a mixture of formulas I and II.

18. An article according to claim 17 wherein said coating composition comprises at least 50% by weight polybenzoylresorcinol of formula I, based on total amount of polybenzoylresorcinols.

19. An article according to claim 17 wherein said coating composition comprises up to about 50% by weight polybenzoylresorcinols.

20. An article according to claim 1 wherein said transparent polymer matrix comprises 2–42% of said polybenzoylresorcinols.

* * * * *